(12) United States Patent
Ghaffari Nik et al.

(10) Patent No.: US 11,397,241 B2
(45) Date of Patent: Jul. 26, 2022

(54) RADIO FREQUENCY LIFE DETECTION RADAR SYSTEM

(71) Applicants: Hossein Ghaffari Nik, Fairfax, VA (US); Desmond A. Fraser, Oak Hill, VA (US); Nathalia Peixoto, Fairfax, VA (US)

(72) Inventors: Hossein Ghaffari Nik, Fairfax, VA (US); Desmond A. Fraser, Oak Hill, VA (US); Nathalia Peixoto, Fairfax, VA (US)

( * ) Notice: Subject to any disclaimer, the term of this patent is extended or adjusted under 35 U.S.C. 154(b) by 0 days.

(21) Appl. No.: 17/076,769

(22) Filed: Oct. 21, 2020

(65) Prior Publication Data

US 2021/0181307 A1   Jun. 17, 2021

Related U.S. Application Data

(60) Provisional application No. 62/924,110, filed on Oct. 21, 2019.

(51) Int. Cl.

| | | |
|---|---|---|
| *G01S 7/41* | (2006.01) | |
| *G01S 13/88* | (2006.01) | |
| *G01S 13/90* | (2006.01) | |
| *H01Q 15/24* | (2006.01) | |
| *A61B 5/0205* | (2006.01) | |
| *H01Q 3/10* | (2006.01) | |

(52) U.S. Cl.
CPC ............ *G01S 7/415* (2013.01); *A61B 5/0205* (2013.01); *G01S 13/885* (2013.01); *G01S 13/887* (2013.01); *G01S 13/9076* (2019.05); *G01S 13/9082* (2019.05); *H01Q 3/10* (2013.01); *H01Q 15/246* (2013.01)

(58) Field of Classification Search
CPC .... G01S 7/415; G01S 13/885; G01S 13/9082; G01S 13/9076; G01S 13/887; A61B 5/0205; H01Q 15/246; H01Q 3/10
USPC .......................................................... 342/90
See application file for complete search history.

(56) References Cited

U.S. PATENT DOCUMENTS 3,327,307 A * 6/1967 Miles ...................... G01S 13/32
                                                        367/101
6,633,254 B1 * 10/2003 Sutphin .................. G01S 7/006
                                                        340/541

(Continued)

FOREIGN PATENT DOCUMENTS

| CA | 2198693 A1 * | 8/1997 | ......... B60R 25/1009 |
|---|---|---|---|
| CA | 2790969 A1 * | 9/2011 | ........... G10L 19/018 |
| EP | 3739356 A1 * | 11/2020 | ............. G01P 15/18 |

OTHER PUBLICATIONS

S. Karthikeyan and N. S. Renga Preethi, "Life detection system using UWB Radar During Disaster," 2018 Second International Conference on Green Computing and Internet of Things (ICGCIoT), Bangalore, India, 2018, pp. 361-365, doi: 10.1109/ICGCIoT.2018.8752992. (Year: 2018).*

(Continued)

*Primary Examiner* — Vladimir Magloire
*Assistant Examiner* — Alexander L. Syrkin
(74) *Attorney, Agent, or Firm* — Capitol Patent & Trademark Law Firm, PLLC

(57) ABSTRACT

Trapped or confined individuals may be located and rescued by detecting their vital signs (e.g., chest movement or heart beat) using reflected, radio frequency signals over a range of multiple antenna polarities.

6 Claims, 7 Drawing Sheets

(56) References Cited

U.S. PATENT DOCUMENTS

| | | | | |
|---|---|---|---|---|
| 10,735,298 | B2* | 8/2020 | Chen | A61B 5/7253 |
| 2004/0263379 | A1* | 12/2004 | Keller | G01S 13/887 |
| | | | | 342/90 |
| 2005/0007882 | A1* | 1/2005 | Bachelor | G10K 11/343 |
| | | | | 367/103 |
| 2009/0073023 | A1* | 3/2009 | Ammar | G01S 17/89 |
| | | | | 342/22 |
| 2009/0271146 | A1* | 10/2009 | Ammar | G01S 7/411 |
| | | | | 702/155 |
| 2010/0265117 | A1* | 10/2010 | Weiss | G01S 13/9058 |
| | | | | 342/55 |
| 2014/0333470 | A1* | 11/2014 | Blodt | G01F 23/284 |
| | | | | 342/124 |
| 2018/0267160 | A1* | 9/2018 | Slemp | G01S 13/931 |
| 2019/0011530 | A1* | 1/2019 | Dowski, Jr. | G01S 3/784 |
| 2020/0003864 | A1* | 1/2020 | Chi | G01S 7/415 |

OTHER PUBLICATIONS

J. Li, L. Liu, Z. Zeng and F. Liu, "Advanced Signal Processing for Vital Sign Extraction With Applications in UWB Radar Detection of Trapped Victims" in IEEE J. of Select. Top. in Appl. Earth Observ. and Rem. Sens., vol. 7, n. 3, pp. 783-791, Mar. 2014, doi: 10.1109/JSTARS.2013.2259801 (Year: 2014).*

H. Wang, J. Cheng, J. Kao and T. Huang, "Review on microwave/millimeter-wave systems for vital sign detection," 2014 IEEE Topical Conference on Wireless Sensorsand Sensor Networks (WiSNet), Newport Beach, CA, USA, 2014, pp. 19-21, doi: 10.1109/WiSNet.2014.6825499. (Year: 2014).*

S. Karthikeyan and N. S. Renga Preethi, "Life detection system using UWB Radar During Disaster," 2018 Second International Conference on Green Computing and Internet of Things (ICGCIoT), Bangalore, India, 2018, pp. 361-365, doi: 10.1109/ICGCIoT.2018.8752992. (Year: 2018).*

Y. Xu, J. Shao, J. Chen and G. Fang, "Automatic Detection of Multiple Trapped Victims by Ultra-Wideband Radar," in IEEE Geoscience and Remote Sensing Letters, vol. 10, No. 6, pp. 1498-1502, Nov. 2013, doi: 10. 1109/LGRS. 2013. 2260854. (Year: 2013).*

H. Ye, "Life Detection Technique in Earthquake Search and Rescue," 2012 Second International Conference on Instrumentation, Measurement, Computer, Communication and Control, Harbin, China, 2012, pp. 664-666, doi: 10.1109/IMCCC.2012.161. (Year: 2012).*

D. Tahmoush and J. Silvious, "Radar polarimetry for security applications," The 7th European Radar Conference, Paris, France, 2010, pp. 471-474. (Year: 2010).*

* cited by examiner

RADIO FREQUENCY LIFE DETECTION RADAR SYSTEM

RELATED APPLICATION

This application claims the benefit of priority from U.S. Provisional Application No. 62/924,110 (the "'110 Application") filed Oct. 21, 2019. This application incorporates by reference the entire disclosure of the '110 Application as if set forth in full herein.

INTRODUCTION

This section introduces aspects that may be helpful to facilitate a better understanding of the described invention(s). Accordingly, the statements in this section are to be read in this light and are not to be understood as admissions about what is, or what is not, in the prior art.

Major natural disasters, such as earthquakes, tsunamis or storms will likely cause infrastructure damage leading to injuries, significant loss of life, and people trapped beneath debris. Typically, immediate search and rescue operations are required in order to save lives because the difference between life and death could be a matter of hours. It is therefore essential for first responders to have a clear understanding of the location and health status of injured and/or trapped individuals. To ascertain such information first responders implement so-called "life detection" techniques such using trained search dogs, radar, optical, acoustic, and infrared life detection systems. In general, life detection systems can be divided into two different categories: active and passive sensing. Search dogs, optical, acoustic and infrared detection systems rely on passive sensing. Typically, passive sensing systems only measure energy or signals that have been transmitted from an external source such as the temperature of a trapped individual.

In comparison, an active sensing system, such as a radar-based detection system, transmits its own source of energy by actively sending a wave of electromagnetic energy towards a target (e.g., trapped individual) and then detecting the amount of backscatter (portion of the originally transmitted signal) that is reflected by an individual, for example, back to the active system.

Generally, existing radar systems rely on multiple transmitter-receiver antenna pairs that are displaced from each other to enable the detection of multiple targets in three dimensions (3D). This need for multiple transmitter-receiver antenna pairs and physical antenna displacement results in large, complex, heavy and expensive equipment. Further, existing radar detection systems only operate effectively over short detection range, have poor multi-target identification and poor positioning capabilities.

Accordingly, it is desirable to provide systems, devices and related methods that overcome the shortfalls of existing techniques.

SUMMARY

The inventors disclose various systems, devices and related methods that may be used to detect individuals, for example, that are trapped beneath collapsed structures or trapped within confined spaces, for example.

One exemplary method may comprise: transmitting radio frequency signals towards a trapped or confined individual from a fixed, rotating transmitter; changing the polarity of one or more of the transmitted signals; receiving one or more reflected signals from the trapped or confined individual at one or more rotating receivers, each reflected signal corresponding to a transmitted signal; and completing a short-time Fourier transform and time frequency analysis to detect movement of the trapped or confined individual based on the received signals.

DETAILED DESCRIPTION, WITH EXAMPLES

Figure 1:
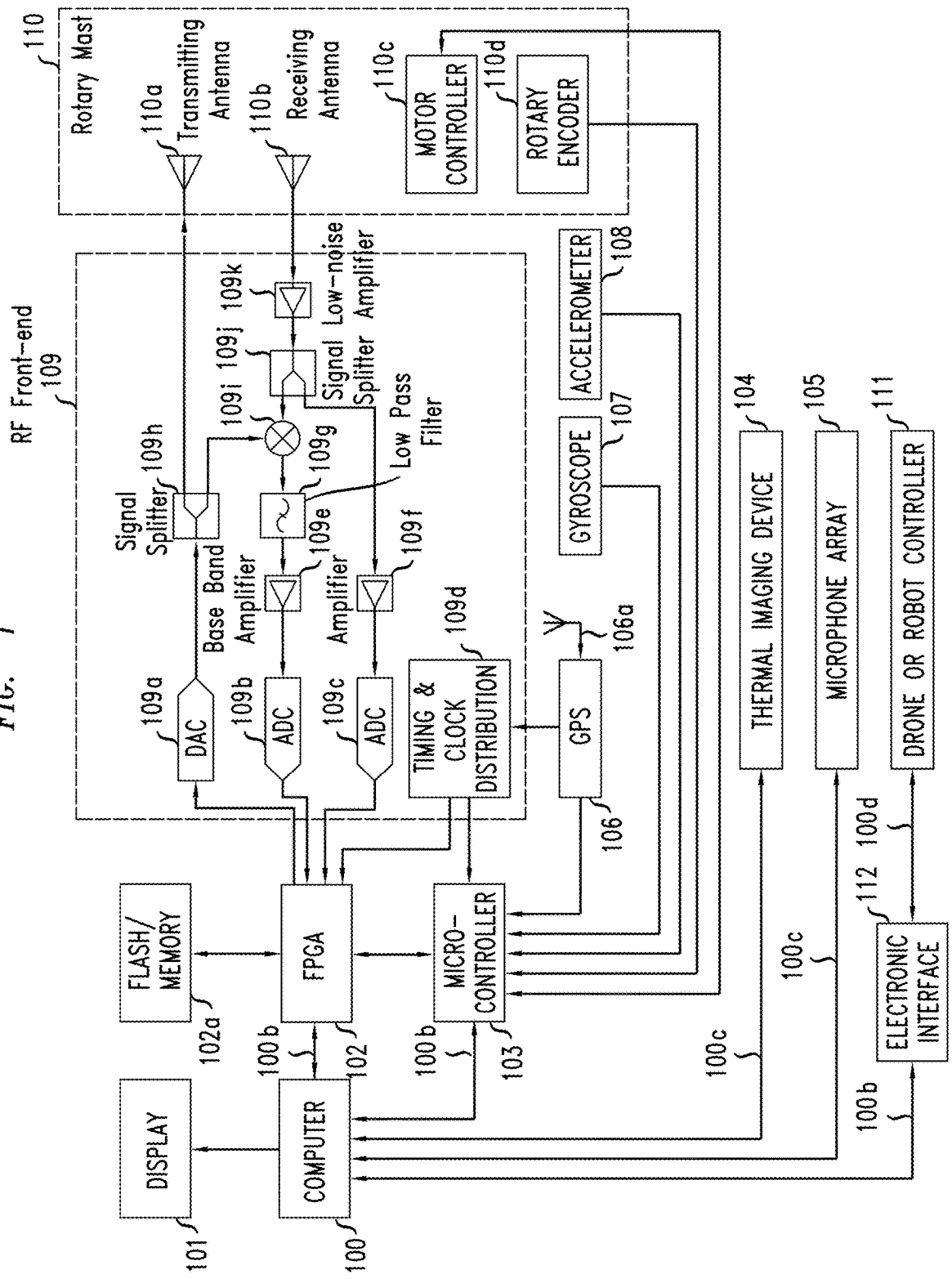
FIG. 1 depicts a simplified block diagram of an exemplary, inventive system according to an embodiment of the invention.

Exemplary embodiments of systems, devices and related methods for detecting individuals that are trapped beneath rubble, for example.

Embodiments of the invention are described herein and are shown by way of example in the drawings. Throughout the following description and drawings, like reference numbers/characters refer to like elements.

It should be understood that although specific embodiments are discussed herein, the scope of the disclosure is not limited to such embodiments. On the contrary, it should be understood that the embodiments discussed herein are for illustrative purposes, and that modified and alternative embodiments that otherwise fall within the scope of the disclosure are contemplated.

It should also be noted that one or more exemplary embodiments may be described as a process or method (the words "method" or "methodology" may be used interchangeably with the word "process" herein). Although a process/method may be described as sequential, it should be understood that such a process/method may be performed in parallel, concurrently or simultaneously. In addition, the order of each step within a process/method may be rearranged. A process/method may be terminated when completed, and may also include additional steps not included in a description of the process/method if, for example, such steps are known by those skilled in the art.

As used herein, the term "and/or" includes any and all combinations of one or more of the associated listed items. As used herein, the singular forms "a," "an" and "the" are intended to include the plural form, unless the context and/or common sense indicates otherwise.

It should be understood that when an system or device, or a component or element of a system or device, is referred to, or shown in a figure, as being "connected" to (or other tenses of connected) another system, device (or component or element of a system or device) such systems, devices, components or elements may be directly connected, or may use intervening components or elements to aid a connection. In the latter case, if the intervening systems, devices, components or elements are well known to those in the art they may not be described herein or shown in the accompanying figures for the sake of clarity.

As used herein the term "operable to" means "functions to" unless the context, common sense or knowledge of one skilled in the art indicates otherwise.

It should be understood that the phrase "computer" and "micro-controller" may comprise one or more electronic processors that are operable to retrieve and execute instructions stored as electronic signals in electronic memory, where a set of such stored instructions may constitute steps in an inventive process or application, or may be executed to complete an inventive function(s) such as rotating, transmitting, receiving, sending, processing, detecting, completed, displayed, sensing, re-processing, re-computing (and tenses of the aforementioned functions) to name just a few inventive functions that may be completed by executing such stored electronic instructions. Further, it should be understood that each embodiment of a computer or micro-controller described herein is further configured with the necessary hardware and firmware components to enable each to process signals and data and/or content (collectively "data") much faster than humanly possible and to receive, transmit and exchange data much faster than humanly possible. Each of the embodiments of the present invention cannot practically be implemented in any amount of time that would be acceptable to one skilled in the art using human beings as substitutes for the systems and devices described herein. For example, the embodiments described herein involve methods that detect the vital signs of individuals, for example, that may be trapped beneath collapsed structures or are trapped within a confined space. Accordingly, the use of humans as substitutes for such methodologies is contrary to the objectives of the invention and does not result in the improvements provided by the invention because, for example, the inventive methodologies process received, reflected signals many times faster than the human mind (within the time periods demanded by users of embodiments of the present invention and those skilled in the art of the present invention).

As used herein, the term "embodiment" or "exemplary" mean an example that falls within the scope of the invention (s).

To overcome the disadvantages of existing radar detection techniques the present inventors provide for, among other things, the use of a single transmitter-receiver pair instead of multiple pairs.

Referring now to FIG. 1, the inventors provide for an inventive, exemplary radar-based life detection system 1 that includes a single rotary, transmitter-receiver antenna pair. By rotating the system 1, multiple polarities with spatial antenna displacement may be used in order to achieve multiple target detection and localization in 3 dimensions (3D) along with the ability to measure the breathing and heartbeat of trapped individuals, for example.

The exemplary system 1 may comprise a portable, accurate, and affordable life detection system. In embodiments of the invention, the system 1 may be a handheld device, or a device that is mounted on a drone or a mobile robot to name just some of the configurations of the exemplary system 1.

In one embodiment the system 1 may comprise a special purpose computer 100 operable to execute instructions stored in a memory to monitor, control, and perform required signal processing for multi-target detection, 3D localization, and vital signs detection using radio frequency (RF) signals, for example. To complete each such feature/function the computer 100 may execute instructions stored in memory, that include, for example, Artificial Intelligence (AI), machine learning and/or deep learning detection processes. In an embodiment, such a process may take the form of stored instructions that complete the steps of one or more neural networks.

Yet further, the system 1 may be separated into individual components. For example, in one embodiment the computer 100 may be located remotely from other components (e.g., subsystems) of the system 1. In such a configuration the computer may using wired or wireless communications such as Wi-Fi, cellular networks (5G for low latency), Bluetooth wireless technology using one or more RF communication protocols.

The exemplary system 1 may also comprise a thermal imaging device 104 and microphone array 105 that may be interfaced 100c with the computer 100. Devices 104, 105 may function as secondary and tertiary life detection systems when used in combination with other features of system 1 in order to increase the accuracy and detection capability of the system 1.

In another embodiment, system 1 may comprise electronic circuitry that functions as an interface 112 to connect computer 100 with a drone and/or mobile robot controller system 111. Such a system 111 may be operable to provide feedback and control signals 100d to system 1 in order to aid in a search and rescue operation.

System 1 may comprise a display 101 that may be an integral part of computer 100, for example, or may be a separate component (not shown). In either case, the display 101 may be operable to display the results of a search and rescue operation and/or control features of the system 1. In an embodiment the computer 100 may execute stored instructions that function as a graphical user interface (GUI). Features of the GUI may be displayed in order to display the results of a search and rescue operation and/or control features of the system 1, for example.

In another embodiment, results may be sent to an augmented reality device and/or wearable glasses/head units (not shown) where the results may be overlaid, for example, on an image from a camera.

Referring back to FIG. 1, a field-programmable gate array circuitry 102 (FPGA) may function as an interface between RF front-end circuitry 109 and the computer 100. In an embodiment, the FPGA may be responsible for generating different RF transmission signals to, and high-speed capture and processing of received (reflected) signals from, the RF front-end circuitry 109. The FPGA 102 may also comprise flash EEPROM and RAM memory 102a (e.g., 1 Gigabit)) that may function to store signals, data, and image processing instructions for accurately locating objects or persons as a part of a search and rescue operation. The FPGA circuitry 102 may also be interfaced with a micro-controller 103 (e.g., 200 Megabits per second). In an embodiment, micro-controller 103 may perform general "housekeeping" functions, such as data collection, and control of various other subsystems. It should be understood that the FPGA 102 and flash/memory 102a may be a separate subsystem of system 1 or, alternatively, may be a part of RF front-end circuitry 109, for example.

In exemplary embodiments, FGPA 102 may generate exemplary Input frequencies from 300 MHz to 8 GHz as well mixer demodulated IF frequencies and may apply one or more modulation schemes, such as continuous wave (CW)-modulation (or unmodulated), frequency and pulse modulation/unmodulated (compressed and/or uncompressed), Intra-pulse or interpose modulation, linear frequency modulation, and/or chirped frequency modulation, for example.

In more detail, the micro-controller 103 may be operable to execute stored instructions to communicate with the computer 100 and the FPGA 102 in order to control various subsystems and exchange data with such subsystems, for example. For example, micro-controller 103 may be operable to exchange instructions (e.g., electrical signals) with a motor controller 110c in order to adjust the rotation of an antenna rotary mast 110. Further, the micro-controller 103 may be operable to receive data representative of the rotational position of the mast 110 from a rotary encoder 110d that is connected to the mast 110. Still further, data from a gyroscope 107 and an accelerometer 108 may also be received by the micro-controller 103. Thereafter, the micro-controller 103 and/or computer 100 may be operable to execute instructions stored in memory to adjust the orientation of the mast 110 due to unwanted movement and vibrations of the system 1 in accordance, for example, with one or more stored processes realized in stored electronic instructions (e.g., target detection processes).

In an embodiment, if the system 1 is to be operated by a live operator in a "handled" mode, a wireless or wired smart sensor (not shown in FIG. 1) may be placed on the operator to collect vital signs such as heart rate and breathing rate in order to filter out signal interference that may cause data collection errors.

Continuing, global positioning system (GPS) circuitry 106 and a GPS antenna 106a may, in combination, be operable to provide global positioning and accurate timing for system-wide clock distribution and synchronization to the micro-controller 103 and the RF front-end 109.

In an embodiment, RF front-end 109 comprises RF analog-to-digital (ADC) 109b, 109c and digital-to-analog (DAC) 109a conversion circuitry/components for automatic gain control of transmitted signals over a wide range of RF power outputs. Digital signals generated by the FPGA 102 may be converted to analog signals through a DAC circuitry 109a, passed through a signal splitter 109h, and then transmitted to an area to be analyzed (e.g., for indications of individuals that are alive or moving) via antenna 110a and to be fed into an electronic mixer 109i.

Signals sent from the transmitting antenna 110a towards a target (e.g., a trapped or confined individual) may be reflected by a target (e.g., possible individuals) and received by the receiving antenna 110b. In an embodiment, the system 1 may comprise a receiver or transceiver operable to receive frequencies over the range of 300 MHz to 80 GHz, for example, and have a dynamic range of 120 dB, for example. The received signal(s) may then be amplified by a low-noise amplifier 109k and then split by a signal splitter 109j. One path of the split signal may be fed into the mixer 109i and mixed with the transmitted signal from splitter 109h. When two signals (e.g., frequencies) are applied to the frequency mixer 109i the mixer 109i may be operable to produce a new signal(s) representing the sum and difference of the original frequencies. The output of the mixer 109i may then be passed through a base band amplifier 109e which filters out portions of the frequencies that relate to the sum of the original frequencies while allowing the difference of the original frequencies (beat frequency) to pass through. In an embodiment, this passed through signal may be an analog signal that is converted to digital form by an ADC 109b and then sent to the FPGA 102. The so converted signal may be further converted to a value that is processed in accordance with a target detection process. The other path of the signal splitter 109j may represent the original signal that was received by the receiving antenna 110b which may be passed through amplifier 109f, converted to digital form via ADC 109c and then sent to the FGPA 102 where a value of the so-converted signal may be processed in accordance with an inventive target detection process.

In an embodiment, timing and clock distribution circuitry 109d may be operable to provide synchronization and coherence to transmitted and received signals used by the DAC 109a, ADCs 109b, 109c, and mixer 109i.

It should be understood that the RF front-end 109 may alternatively be implemented in software stored as instructions (electrical signals) and/or with additional transmission and receiving paths for additional transmitting and receiving antennas.

The rotary antenna mast 110, 200 may house the transmitting antenna 201 and receiving antenna 202. In embodiments of the invention, the system 1 provides multiple antenna positions and antenna polarities 205 by rotating the mast 206 from 0 to 360 degrees, for example. In embodiments, the mast may be controlled and rotated by the computer 100 or micro-controller 103 such that the rotational speed of the mast may vary. For example, the amount of electrical or physical interference within a reflected signal and/or the accuracy needed to positively detect a trapped individual may determine whether the speed of the mast may be increased or decreased, for example.

Yet further, the speed of the mast may be controlled such that the mast rotates at a pre-determined speed initially (e.g., a first mode of operation). Thereafter, the speed of the mast may be reduced (i.e., a second mode of operation) when a potential target has been located. Still further, another mode of operation may allow the polarity of the signal being transmitted from the mast to be varied.

Figure 2A:
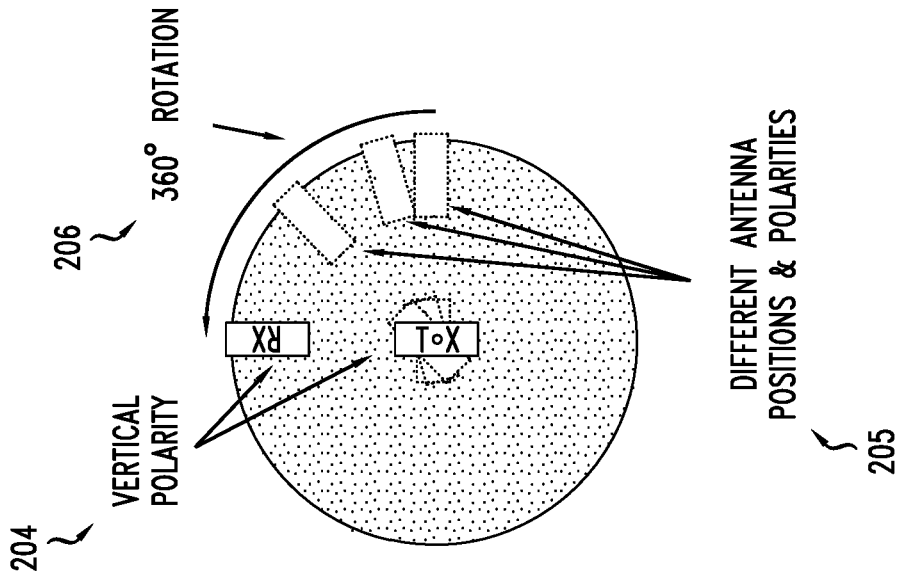
FIGS. 2A and 2B depict exemplary positions of an inventive antenna according to embodiments of the invention.
Figure 2B:
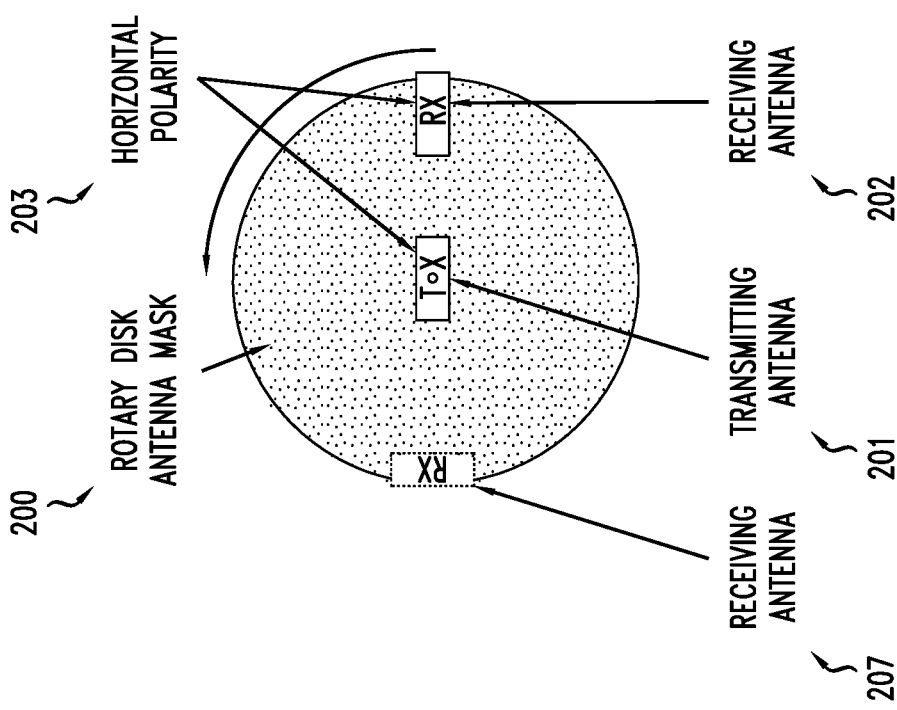

As shown in FIGS. 2A and 2B, in an embodiment the transmitting antenna 201 may be located at the center of the mast 206 and its position fixed while its polarity may be continuously changed between a vertical 204 and horizontal 203 polarity. In contrast, the receiving antenna 202 may be off-centered and located toward the edge of the mast 206 where both its position and polarity may continuously change between vertical 204 and horizontal 203.

In an embodiment, by rotating and displacing the antenna multiple vantage points for the receiving antenna are created. Thus, the rotating antenna can be said to "mimic" multiple, physical receiving antennas.

In an alternative embodiment, a secondary receiving antenna 207 at a different polarity and location compared to the first receiving antenna 202 may be utilized to provide better detection and accuracy. Thus, one or more rotating receiving antenna may be used.

The configuration, location, and orientation of the transmitting antenna 201 and receiving antenna 202, 207 may be different, as illustrated in FIGS. 2A and 2B. Because RF signals propagate differently through obstacles (e.g., human beings) at different polarities, the ability for the inventive system 1 to sweep through a plurality of RF/antenna polarities in order to detect a trapped individual, for example, is advantageous.

In an embodiment, to determine the location of a trapped individual, the received, reflected signals may be processed in accordance with a multi-target detection and localization process that may be implemented by computer 100 and FGPA 102. The inventive process detects multiple targets (trapped individuals) and their vital signs (heartbeat, breathing) with 3D localization using multiple RF signal profiles and different antenna positions and polarities through, among other things, data provided by the rotary antenna mast 110. The system 1 may use multiple RF signal profiles, i.e. continuous wave (CW), frequency modulated continuous wave (FMCW), pulsed, random noise and/or any combination of such profiles.

Figure 3:
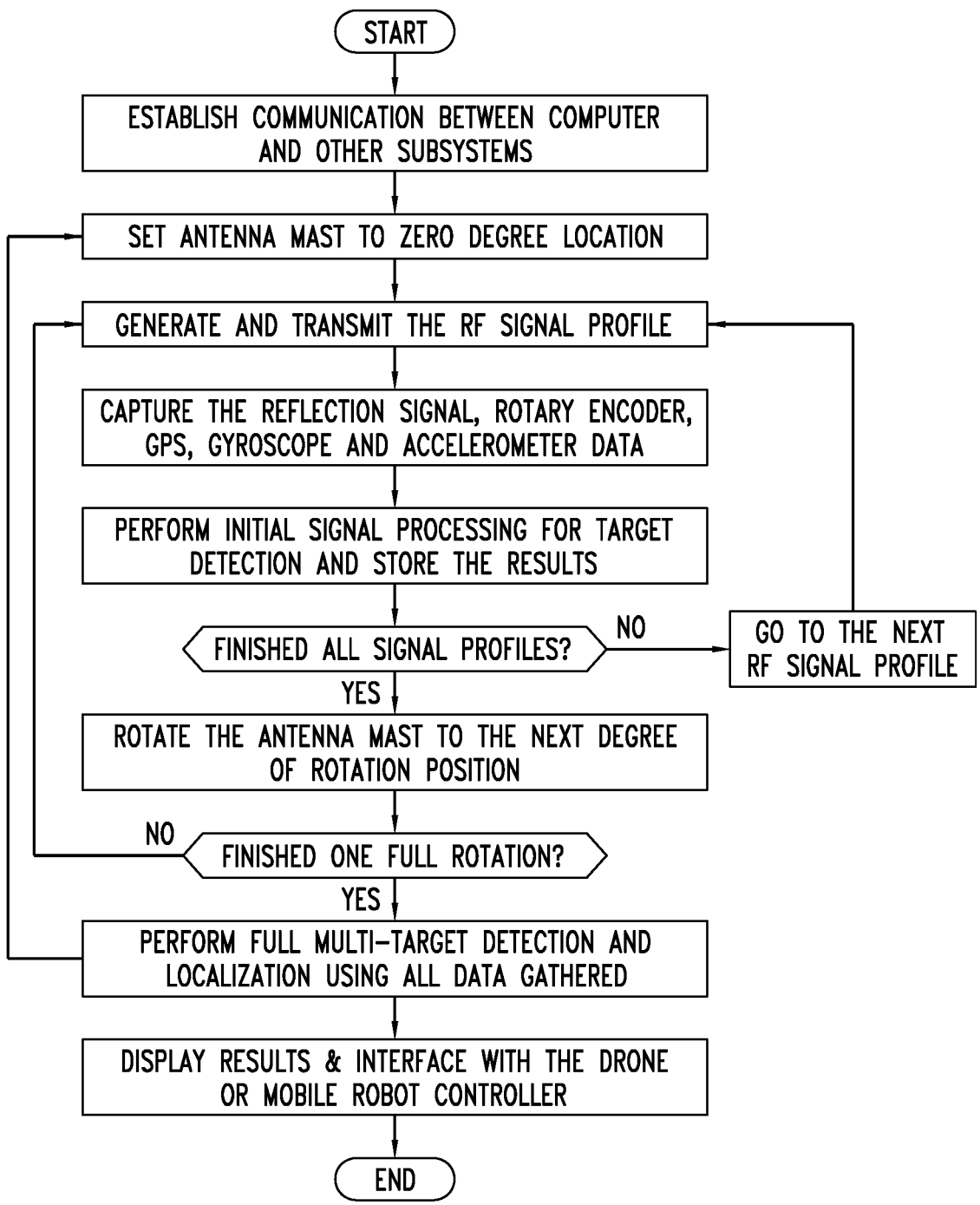
FIG. 3 depicts an exemplary flow diagram of a multi-target detection and localization process according to an embodiment of the invention.

FIG. 3 illustrates exemplary features and steps in such an inventive process. The exemplary process illustrated by FIG. 3 may begin by establishing communications between the computer 100 and other subsystems and then initializing the antenna rotary mast 110 to a zero-degree rotational position.

A first RF signal profile (signals having a range of frequencies, modulations, polarities, for example, 300 MHz to 80 GHz and one or more modulation schemes such as CW modulation or unmodulated, frequency and pulse modulation/unmodulated (compressed and uncompressed), intra-pulse or interpose modulation, linear frequency modulation, and chirped frequency modulation) may be transmitted by the FPGA 102 towards suspected targets (e.g., trapped individuals) using the RF front-end 109 and the transmitting antenna 110*a*. The so-transmitted RF signals propagate through the air until a target is reached, whereupon the target may reflect a portion of the signal back towards the receiving antenna 110*b*. Upon being received, the reflected signal(s) may be sent to the FPGA 102 through the RF front-end 109. This signal and other data, such as the rotary encoder position, GPS data/clock, gyroscope, and accelerometer data may then be received and stored by the micro-controller 103 (collectively "received data").

In an embodiment, a stored inventive, multi-target detection and localization process comprising instructions (stored electronic signals) is then executed by computer 100 to complete initial signal processing of the received data. Thereafter, the computer 100 executes further stored instructions that are a part of the inventive process to complete steps in sets of different RF signal profiles at each rotation position of the antenna mast.

In an embodiment, the micro-controller 103 may execute the same instructions for each RF signal profile at each rotational position to complete one full rotation.

To account for unwanted reflections (i.e., clutter) from stationary objects/targets, such as rocks and rubble, such reflections may be electronically detected and separated from reflections that originate from trapped individuals that are moving (though sometimes the movement is slight). The movement and vibration data that is part of the received data can be used to aid false-positive detection of stationary objects/targets. The multi-target detection and localization process comprises full signal processing on all received data for each RF signal profile and all rotation positions.

In an embodiment, detection results of multiple targets, their vital signs and 3D locations may be displayed on display 101 and/or be forwarded or sent to a drone or mobile robot controller 111.

Experimental Set-Up

Figure 4:
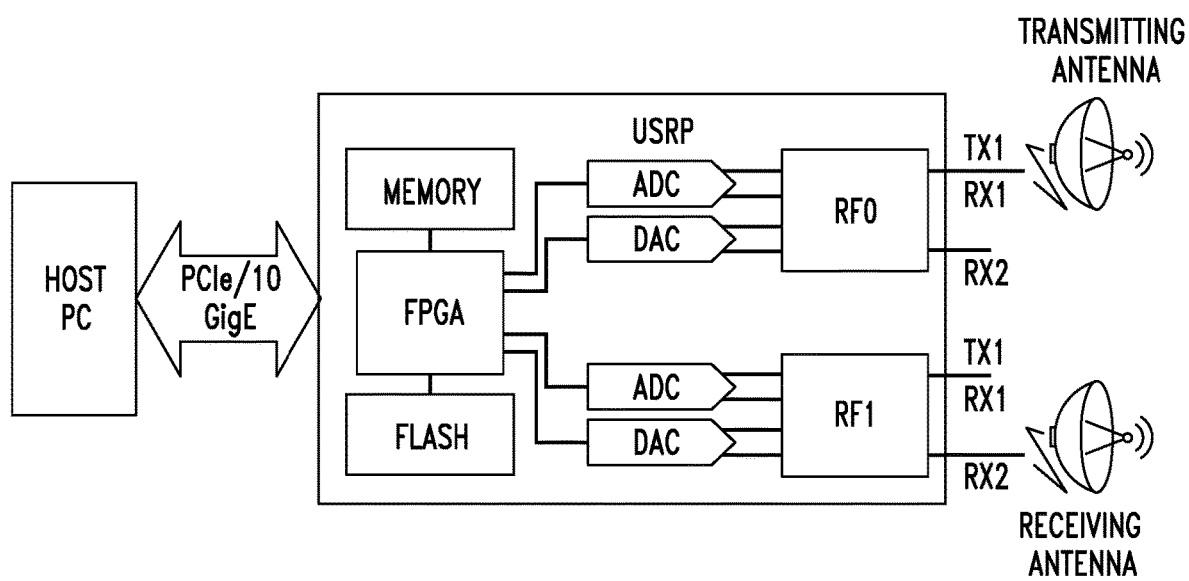
FIG. 4 depicts an exemplary, experimental radar system according to an embodiment of the invention.

In an experiment conducted by the inventors a high-performance universal software radio peripheral (USRP) by National Instruments (NI) which includes 2×2 MIMO transceivers (R0, R1) or four-channel superheterodyne receivers and an onboard field-programmable gate array (FPGA) were used as an exemplary, inventive radar-based life detection system (see FIG. 4).

The NI USRP 2944-R transmitter-receiver (transceiver) had a tunable bandwidth of nearly 6 GHz with frequency range of 10 MHz to 6 GHz with signal bandwidth of 160 MHz on the carrier frequencies, with two full duplex channels. The USRP used a powerful Xilinx Kintex 7-410T FPGA for advanced digital signal processing (DSP) and was controlled via a host computer through PCIe® Gen3 and 10 Gigabit Ethernet GigE (or 100*b*) for maximum data streaming bandwidth of 200 MS/s. The programming and control of this USRP was done via the host computer using LabVIEW® and LabVIEW® FPGA Module (National Instruments—Austin, Tex.).

The antenna used was a 2 GHz to 11 GHz printed circuit board (PCB) Log Periodic (LP) antenna model number WASVJB suitable for frequency sweeps and other broadband applications.

The experimental radar was setup in a bistatic, CW configuration for simultaneous transmitting and receiving.

The inventors generated an exemplary waveform for the radar using a LabVIEW program on the host computer and constantly streamed this data to the USRP transceiver to be transmitted (TX1). In full duplex mode, the receiver (RX1, RX2) of the USRP simultaneously received the reflected signals and constantly streamed the data representing the reflections back to the host computer. The host computer executed instructions that functioned as a signal mixer by, for example, multiplying the transmitted signal with the complex conjugate of the received signal to detect the frequency difference between the two signals. Thereafter, the host computer executed instructions to complete an inventive, multi-target detection and localization process. In an embodiment, one such process that was competed comprised a short-time Fourier transform (STFT) and time frequency analysis (TFA) for detecting and displaying movement of a target (e.g., trapped individual).

In an embodiment, to more precisely detect the movement of a target, RF signals may be represented by I/Q data where I is the in-phase signal component and Q is the quadrature signal component. In more detail, each sample of a signal to be generated or measured may be characterized by computing a peak amplitude times cosine of some phase angle—$A \cdot \cos(\phi)$. Instead of looking at the signal as a flat curve in two dimensions of amplitude and time, the inventors represent the signal as a spiral in three dimensions of amplitude, phase, and time. The I/Q data is just a translation of amplitude and phase data from a polar coordinate system to the cartesian coordinate system. Equation (1) may be used for translating I/Q signals between polar and rectangular form:

$$A = \sqrt{I^2 + Q^2}$$

$$\phi = \tan^{-1}(Q/I)$$

$$I = A \cdot \cos(\phi) \quad Q = A \cdot \sin(\phi) \tag{1}$$

where A is the amplitude, $\phi$ is the phase, I is the real original signal, and Q is the real signal phase shifted by −90°. Equation (2) is the Euler form representation of the signal from I/Q or amplitude and phase:

$$A \cdot e^{i\phi} = A \cdot (\cos(\phi) + i \cdot \sin(\phi)) = 1 + Qi \tag{2}$$

FMCW Radar

Figure 5:
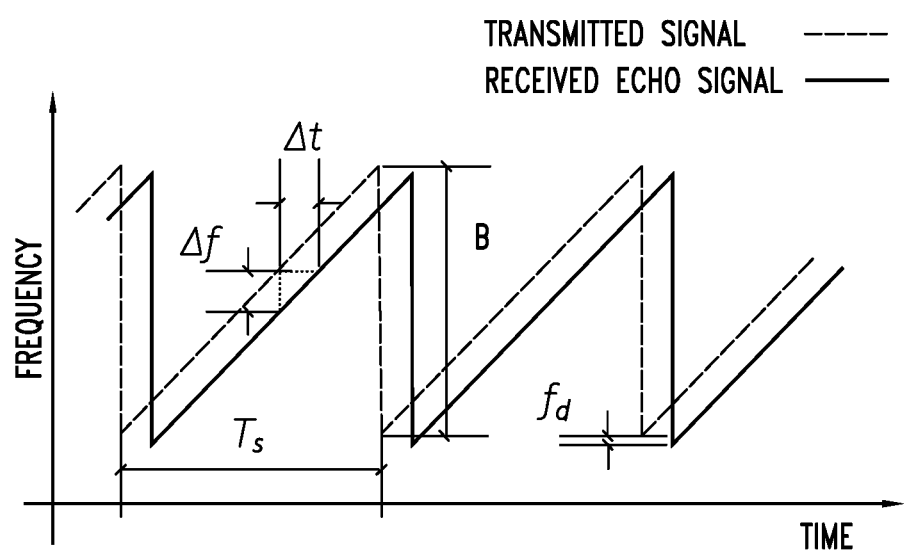
FIG. 5 illustrates the principals of ranging of a radar.

A CW radar can detect movements of a target through shifts in the frequency due to the Doppler Effect, but is unable to determine the range to the target. FMCW radar is an extension of a CW radar where the frequency of the transmitted signal is modulated and changing in time. As such, the frequency of the signal increases or decreases periodically. This enables the detection of both relative velocity and range to the target. The frequency of a transmitted signal is known and when a reflected signal is received the change in frequency is delayed due to time of flight to the target and back. FIG. 5 illustrates the principals of ranging with a saw tooth linear FMCW radar.

Equation 3 calculates the range to target from a linear FMCW radar:

$$R = \frac{c \cdot |\Delta t|}{2} = \frac{c \cdot T_s \cdot |\Delta f|}{4B} \quad (3)$$

where R is the range to target in meters, $T_s$ is sweep time in seconds, $\Delta t$ is delay time in seconds, $\Delta f$ is the instantaneous measured frequency difference in Hz, and B is the sweep bandwidth in Hertz (Hz). If the target has a radial velocity, the Doppler frequency shift can also be measure and used to calculate the velocity using equation (4):

$$f_d = \frac{2v_r}{\lambda} = \frac{2v \cdot \cos\theta}{\lambda} = \frac{(2v \cdot \cos\theta)f_T}{c} \quad (4)$$

The sweep time can be determined based on the time needed for the signal to travel the unambiguous maximum range. In general, for an FMCW radar system, the sweep time should be at least 5 to 6 times the round trip time of the maximum range.

Range resolution of a linear FMCW radar defined as the minimum distance between two targets where the radar can differentiate between the two is expressed as:

$$\Delta r = c/2B \quad (5)$$

The linearly frequency modulated transmitted signal created by the waveform generator (host) can be expressed as:

$$s_T(t) = A_T(t) \cdot \cos(\phi_T(t)),$$

$$-T_s/2 \leq t \leq T_s/2,$$

$$\phi_T(t) = 2\pi f_c \cdot t + \pi B/T_s \cdot t^2 \quad (6)$$

where $A_T(t)$ the amplitude and HO is the phase of the transmitted signal at time t and $f_c$ is the sweep center frequency in Hz. The $s_T(t)$ sweeps from $f_c$−B/2 to $f_c$+B/2 in $T_s$ seconds and is radiated toward the target by the transmitting antenna and a sample of it is also passed through a multiplier (mixer).

The reflected signal from the target may be received by a receiving antenna and enters the same mixer with a time delay of T seconds. Received signal is mixed with a copy of the transmitted signal which results in difference and sum of frequencies of the signals. Sum term is about twice the carrier frequency and is filtered out. Difference term is of a lower frequency, usually few kHz, and contains the information about the target. The mixed signal can be expressed as:

$$s_M(t) = A_M(t) \cdot \cos\left(2\pi\left(\frac{B\tau}{T_s}t - \frac{B\tau^2}{2T_s} + f_c\tau\right)\right) \quad (7)$$

The first term in the cosine function in (7) is the frequency of the mixed signal and is the difference of the transmitted and received frequency. This is also known as the beat frequency. The beat frequency is directly related to the range of the target as expressed by (7). If target is moving the beat frequency will in turn be modulated based on the Doppler frequency shifts. The next two terms in the cosine function in (7) correspond to the phase of the mixed signal. This phase angle can also be used to extract target's range information. The second argument with $\tau^2$ is called the residual video phase, it is very small and can often be ignored. On the other hand, the third term in the cosine function of (7) can be expanded as:

$$f_c \tau = f_c \frac{2R}{c} = \frac{2R}{\lambda} \quad (8)$$

where λ is the wavelength of the sweep center frequency $f_c$. It is possible to detect very small changes to the range of the target within the unambiguous range of λ/2 using the phase. This resolution depends on radar's phase noise and closely located targets cannot be resolved separately. An exemplary linear FMCW radar system operating at $f_c$ of 5 GHz would have a half-wavelength of 30 mm. With the assumption that one-degree resolution on measurement of phase angle is possible, an inventive system would have a theoretical minimum detectable movement of about 83 μm.

Experimental Results

The inventors used the Phased Array System Toolbox™ from MATLAB® to test the theoretical range and movement detection capabilities of an inventive, ideal linearly FMCW radar system. Phased Array System Toolbox™ provides algorithms and apps for the design, simulation, and analysis of sensor array systems in radar, wireless communication, EW, sonar, and medical imaging applications. The inventors implemented an inventive, linear FMCW radar system operating at center frequency of 5.6 GHz (wavelength of 53 mm) with sweep bandwidth frequency of 150 MHz, providing us with 1 m range resolution. The system was setup with a maximum range of 50 m and a sweep time of 1.83 μs. The inventive radar system was modeled to be stationary and parallel to the ground at the height of 50 cm. A target was modeled at the same height in the line of sight of the radar system at the range of 10 m with a periodic movement toward to and away from the radar on the plane of radar's line of sight. The target was simulated to move ±200 μm at the frequency of 0.3 Hz for breathing in addition to amplitude modulation of ±100 μm at the frequency of 1.5 Hz for heartbeats. The transmitted signal was mixed with the reflections received. The beat frequency was estimated through root MUSIC (MUltiple Signal Classification) algorithm.

Figure 6A:
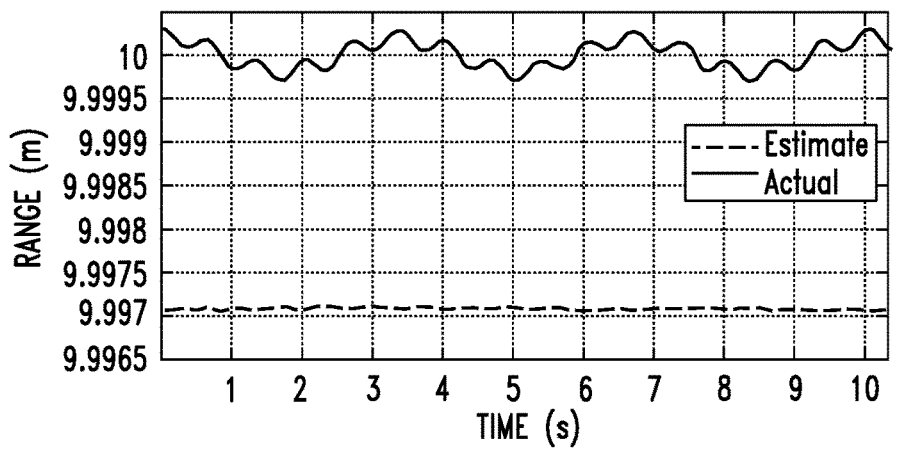
FIGS. 6A to 6C depict experimental results produced by an inventive system.
Figure 6B:
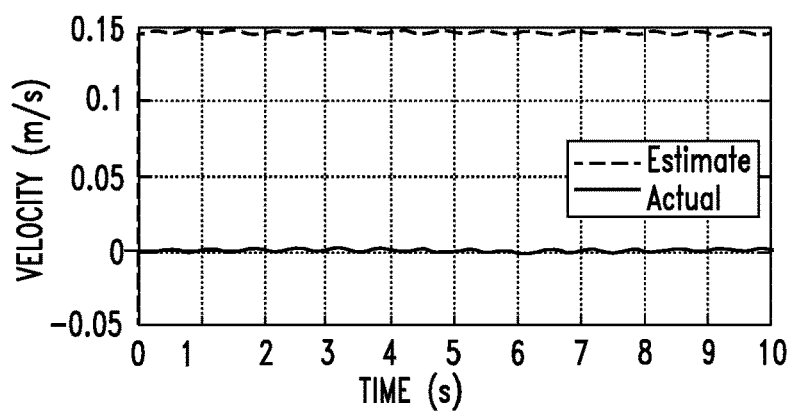
Figure 6C:
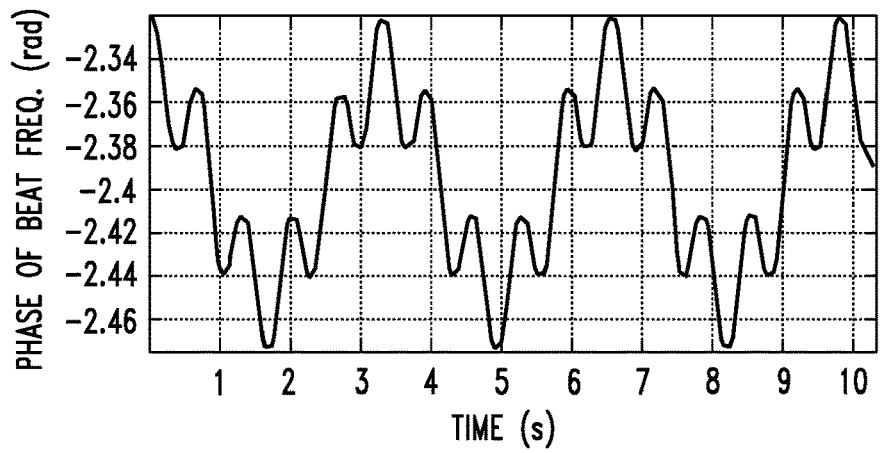

The relative changes to the phase of the detected beat signal provided clear and precise range deviations related to the micro-movements. FIGS. 6A to 6C graphically present experimental results produced by an inventive system.

USRP Preliminary Results

Figure 7:
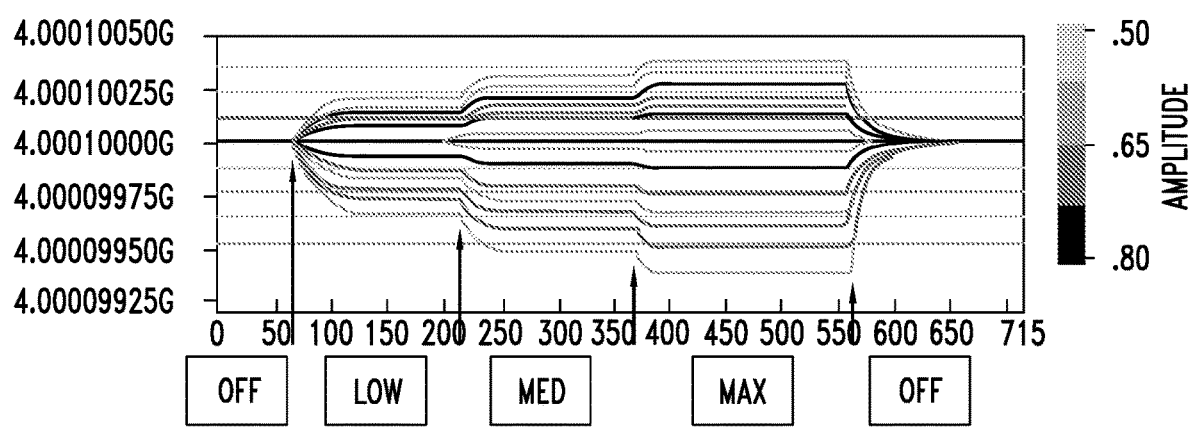
FIG. 7 depicts exemplary detection of micro-Doppler frequency shift effects using an inventive system according to an embodiment of the invention.

The inventors experimented and used LabVIEW® NI-USRP API, USRP RIO Instrument Design Library (IDL), and LabVIEW® FPGA Module in testing of an inventive CW and FMCW radar system operating at 4 GHz for target and movement detection. The inventors were able to detect and display the micro-Doppler effects of a multi-speed rotating metal fan at 1 meter from the FMCW radar system operating at 4 GHz. The inventors were able to detect and visualize the effects from four different operational stages of the fan movement. FIG. 7 depicts the frequency shifts as the fan transitions from off to low, medium and maximum speed to off again.

Using the same setup, the inventors were also able to detect movement related to breathing using our radar from an individual seated 2 meters from the system by analyzing the relative phase shifts on the detected beat frequency.

It should be understood that the foregoing description only describes a few of the many possible embodiments that fall within the scope of the inventions.

For example, in additional embodiments, an inventive system may comprise an FPGA that includes 1 Gigabit of dynamic random-access memory and onboard flash memory. This allows the inventive system to transfer a waveform into the onboard memory once and continuously transmit it directly from the FPGA, thereby reducing the processing required by a computer, for example. This also enables the incorporation of digital RF mixers on the FPGA which further reduces the signal processing required by the host computer.

Numerous changes and modifications to the embodiments disclosed herein may be made without departing from the general spirit of the invention, the scope of which is best defined by the claims that follow.

The invention claimed is:

1. A method for detecting vital signs of a trapped or confined individual using one or more neural networks comprising:
    rotating a co-located antenna of a receiver and rotating a co-located antenna of a transmitter to a plurality of different antenna positions and antenna polarities;
    transmitting a first set of modulated, radio frequency (RF) signals towards the trapped or confined individual from the transmitter connected to the transmitting, rotating antenna at a first antenna position of the plurality of antenna positions using the antenna polarities and a first RF signal profile comprising different modulation types;
    receiving reflected signals from the trapped or confined individual at the rotating receiver connected to the receiving, rotating antenna corresponding to the first set of modulated RF signals;
    further transmitting one or more next sets of modulated, RF signals towards the trapped or confined individual from the transmitter connected to the transmitting, rotating antenna at the first antenna position using the antenna polarities, and a next, different RF signal profile comprising the different modulation types;
    receiving reflected signals from the trapped or confined individual at the rotating receiver connected to the receiving, rotating antenna corresponding to each next set of modulated RF signals;
    repeating the transmission and reception steps for each next antenna position of the plurality of antenna positions;
    receiving signals from a thermal imaging sensor and a camera to further detect the vital signs of a trapped or confined individual;
    combining all of the received reflected signals from the first and each next antenna position, and vital signs detected by the thermal imaging sensor and camera; and
    completing an analysis using all of the reflected signals from the first and each next antenna position, including a phase and frequency analysis, and vital signs detected from the thermal imaging sensor and camera to detect movement of the trapped or confined individual using the one or more neural networks based on: (1) changes in the phase and frequency differences of the reflected, received signals at each of the plurality of different antenna positions and polarities; and (2) the detected vital signs.

2. The method as in claim 1 where the different modulation types comprise pulse modulation, continuous wave modulation and frequency modulation.

3. The method as in claim 1 wherein the antenna positions of the rotating, co-located antenna of the fixed, rotating receiver and the rotating, co-located antenna of the fixed, rotating transmitter comprise from 0 to 360 degrees.

4. The method as in claim 1 further comprising:
    rotating the co-located antenna of the receiver and rotating the co-located antenna of the transmitter to the same antenna position and antenna polarity.

5. A method for detecting vital signs of a trapped or confined individual using one or more neural networks comprising:
    rotating an antenna of a receiver to a plurality of different antenna positions and antenna polarities and fixing an antenna of a transmitter at an antenna position and antenna polarity;
    transmitting a first set of modulated, radio frequency (RF) signals towards the trapped or confined individual from the transmitter using a first RF signal profile comprising different modulation types;
    receiving reflected signals from the trapped or confined individual corresponding to the first set of modulated RF signals at the rotating receiver connected to the receiving, rotating antenna at a first antenna position of the plurality of antenna positions, each reflected signal corresponding to the one of the modulated, transmitted signals;
    further transmitting one or more next sets of modulated, RF signals towards the trapped or confined individual from the transmitter using a next, different RF signal profile comprising the different modulation types;
    receiving reflected signals from the trapped or confined individual at the rotating receiver connected to the receiving, rotating antenna corresponding to each next set of modulated RF signals;
    repeating the transmission and reception steps for each next antenna position of the plurality of antenna positions of the antenna of the receiver;
    receiving signals from a thermal imaging sensor and a camera to further detect the vital signs of a trapped or confined individual;
    combining all of the received reflected signals from the first and each next antenna position, and vital signs detected by the thermal imaging sensor and camera; and
    completing an analysis using all of the reflected signals from the first and each next antenna position, including a phase and frequency analysis, and vital signs detected from the thermal imaging sensor and camera to detect movement of the trapped or confined individual using the one or more neural networks based on: (1) changes in the phase and frequency differences of the reflected, received signals at each of the plurality of different antenna positions and polarities; and (2) the detected vital signs.

6. A method for detecting vital signs of a trapped or confined individual using one or more neural networks comprising:
    rotating an antenna of a transmitter to a plurality of different antenna positions and antenna polarities and fixing an antenna of a receiver at an antenna position and antenna polarity;

transmitting a first set of modulated, radio frequency (RF) signals towards the trapped or confined individual from the transmitter connected to the transmitting, rotating antenna at a first antenna position of the plurality of antenna positions using the antenna polarities and a first RF signal profile comprising different modulation types;

receiving reflected signals from the trapped or confined individual corresponding to the first set of modulated RF signals at the receiver, each reflected signal corresponding to the one of the modulated, transmitted signals;

further transmitting one or more next sets of modulated, RF signals towards the trapped or confined individual from the transmitter connected to the transmitting, rotating antenna at the first antenna position using the antenna polarities, and a next, different RF signal profile comprising the different modulation types;

receiving reflected signals from the trapped or confined individual at the receiver corresponding to each next set of modulated RF signals;

repeating the transmission and reception steps for each next antenna position of the plurality of antenna positions of the antenna of the transmitter;

receiving signals from a thermal imaging sensor and a camera to further detect the vital signs of a trapped or confined individual;

combining all of the received reflected signals from the first and each next antenna position, and vital signs detected by the thermal imaging sensor and camera; and completing an analysis using all of the reflected signals from the first and each next antenna position, including a phase and frequency analysis, and vital signs detected from the thermal imaging sensor and camera to detect movement of the trapped or confined individual using the one or more neural networks based on: (1) changes in the phase and frequency differences of the reflected, received signals at each of the plurality of different antenna positions and polarities; and (2) the detected vital signs.

* * * * *